United States Patent [19]

Goralski et al.

[11] 4,014,891

[45] Mar. 29, 1977

[54] PROCESS FOR MAKING ARYL CHLOROMETHYL SULFIDES

[75] Inventors: Christian T. Goralski, Midland; George A. Burk, Bay City, both of Mich.

[73] Assignee: The Dow Chemical Company, Midland, Mich.

[22] Filed: Jan. 17, 1975

[21] Appl. No.: 540,734

[52] U.S. Cl. .................... 260/302 SD; 260/302 A; 260/302 S; 260/306; 260/309.6; 260/294.8 G; 260/307 D; 260/283 S; 260/556 AR; 260/609 E; 260/609 F

[51] Int. Cl.$^2$ ............. C07C 148/00; C07C 149/34; C07D 277/36

[58] Field of Search ...... 260/609 E, 302 S, 302 SD, 260/306, 307 D, 283 S, 294.8 G, 609 F, 302 A, 309.6

[56] References Cited

UNITED STATES PATENTS

| 2,776,977 | 1/1957 | D'Amico | 260/306 |
| 3,669,981 | 6/1972 | Pera et al. | 260/306 |

FOREIGN PATENTS OR APPLICATIONS 1,227,144   4/1971   United Kingdom

OTHER PUBLICATIONS

Babayan et al., Chemical Abstracts, vol. 55, 11342g (1961).
Herriott, Synthesis, p. 447 (July 1975).

*Primary Examiner*—Nicholas S. Rizzo
*Assistant Examiner*—Diana G. Rivers
*Attorney, Agent, or Firm*—L. Wayne White

[57] ABSTRACT

The title compounds are prepared in excellent yields by reacting an alkali aromatic mercaptide with bromochloromethane in the presence of a quaternary ammonium salt having ten or more carbon atoms. Normally the chlorobromomethane is used in excess as the liquid reaction medium. Reaction temperatures are normally selected in the range of from about 20° to about 65° C.

14 Claims, No Drawings

PROCESS FOR MAKING ARYL CHLOROMETHYL SULFIDES

BACKGROUND OF THE INVENTION

The aromatic mercaptans are a known class of compounds having many members. Various members of the group have heretofore been converted to the corresponding aryl chloromethyl sulfides by various procedures. German Patent 845,511 describes the preparation of aryl chloromethyl sulfides by treating 1 mole of an aromatic mercaptan with at least 1 mole of formaldehyde in the presence of hydrogen chloride. Dolman et al., *Rec. Trav. Chim.*, 88, 417(1969), describe the reaction of 1 mole of an aromatic mercaptan with 1 mole of formaldehyde in the presence of a catalytic amount of sodium methoxide to give the corresponding aryl hydroxymethyl sulfide which is subsequently reacted with 1.1 mole of thionyl chloride to afford the corresponding aryl chloromethyl sulfide. Senning and Lawesson, *Acta Chem. Scand.*, 16, 117(1962), describe the preparation of pentachlorophenyl chloromethyl sulfide by the chlorination of pentachlorophenyl methyl sulfide with chlorine in refluxing carbon tetrachloride.

The aryl chloromethyl sulfides are useful as pesticides. The aryl chloromethyl sulfides are also excellent alkylating agents due to the lability of the chlorine atom in nucleophilic displacements. For example, the aryl chloromethyl sulfides have been heretofore reacted with potassium thiocyanate in acetone to give the corresponding (arylthio)methyl thiocyanates which are excellent fungicides (Dolman et al., supra).

SUMMARY OF THE INVENTION

We have now discovered that the aryl chloromethyl sulfides can be prepared in excellent yield and purity by reacting by contacting in liquid phase.

a. an alkali metal aromatic mercaptide having at least one mercapto group, b. at least one equivalent of bromochloromethane per mercapto equivalent in (a), and c. a small but sufficient amount of a quaternary ammonium salt to catalyze the reaction between (a) and (b); said quaternary ammonium salt having a carbon content of at least 10 carbon atoms.

DETAILED DESCRIPTION OF THE INVENTION

As noted above, the aromatic mercaptans form a known class of compounds, each member of which has at least one mercapto (—SH) group attached directly to the aromatic nucleus. The aromatic nucleus may be a carbocyclic nucleus or a heterocyclic nucleus containing nitrogen, sulfur and/or oxygen as well as carbon atoms within the heterocyclic ring. The aromatic nucleus may be a single aromatic ring or it may be a fused ring system. Examples of such aromatic mercaptans include those wherein the aromatic nucleus is benzene, biphenyl, thiazole, oxazole, isothiazole, thiadiazole, pyridine, imidazole, and the like, and inertly-substituted derivatives thereof. By "inertly-substituted" is meant any substituent(s) that is inert in the instant process. Examples of such inert substituents include halo groups, hydrocarbyl groups, hydrocarbyloxy groups, etc. Specific examples of such aromatic mercaptans therefore include: phenyl mercaptan, tolyl mercaptan, chlorophenyl mercaptan, biphenyl mercaptan, naphthalenyl mercaptan, anthracenyl mercaptan, 2-mercaptobenzothiazole, etc. and bis-mercaptans, such as 1,3bismercaptobenzene, 4,4'-bismercaptodiphenyl, 4,4'-bismercaptodiphenyl oxide, etc. and other like aromatic compounds bearing at least 1 mercapto group. Aromatic mercaptans bearing from 1 to 3 or more mercapto groups per aromatic nucleus are known (and are suitable for use herein) but the most common (and therefore preferred) species bear 1 or 2 mercapto groups per aromatic nucleus.

The alkali metal aryl mercaptides are easily produced by reacting the aromatic mercaptan with at least one equivalent of alkali metal hydroxide per aryl mercapto group. In the instant process, the alkali metal aryl mercaptides can be preformed and used as the isolated salt, or, they can be generated in situ by merely combining the mercaptan and alkali metal hydroxide in the instant reaction mixture. The latter technique is preferred.

Essentially any one of the alkali metal hydroxides can be used in the instant reaction (e.g. lithium hydroxide, potassium hydroxide, sodium hydroxide, etc.) but we currently prefer to use sodium or potassium hydroxide and most prefer potassium hydroxide. Such hydroxides are, of course, solid and we have found it most convenient to use them in a finely divided form (i.e., powdered). Bromochloromethane is a known compound which is normally liquid (b.p. 69° C.). The stoichiometry of the instant reaction requires one mole of bromochloromethane per mercapto group on the aromatic mercaptan reactant. We prefer to use the bromochloromethane in substantial excess as the liquid reaction medium since it normally is a solvent for the aromatic mercaptans.

The process is conducted in the presence of a small but catalytic amount of a quaternary ammonium salt having an aggregate carbon content of at least 10 carbon atoms (preferably from about 12 to about 31 carbon atoms). It was noted that such ammonium salts were normally soluble in the chlorobromomethane. The examples of suitable such ammonium salts include tetraalkylammonium salts, such as tetra-n-butyl-, tetrahexyl-, tri-n-butylmethyl-, tri-octylmethyl- and tridecylmethylammonium chlorides, bromides, bisulfates, tosylates, etc.; aralkyl ammonium salts, such as the tetrabenzyl-, benzyltrimethyl-, benzyltriethyl- and benzyltributylammonium chlorides, bromides, methylsulfates, etc.; aryl ammonium salts, such as triphenylmethylammonium fluoride, chloride or bromide, N,N,N-trimethylanilinium bromide, N,N-diethyl-N-ethylanilinium bisulfate, trimethylnaphthylammonium chloride, p-methylphenyl trimethyl ammonium chloride or tosylate, etc.; 5-and 6-membered heterocyclic compounds containing at least one quaternized nitrogen atom in the ring, such as N-hexylpyridinium iodide, 4-pyridyltriethyl ammonium chloride, N,N-dibutyl morpholinium chloride, etc., and other like compounds.

The preferred ammonium salts are the benzyltrimethyl, benzyltriethyl, tetra-n-butyl and tri-n-butylmethylammonium salts. The most preferred salts are benzyltriethylammonium salts and tetra-n-butylammonium salts.

The ammonium salts are here used in small but catalytic amounts. For example, amounts of from about 0.25 up to about 20 mole percent of the ammonium salt, based on the aromatic mercaptan compound, have resulted in satisfactory reaction rates.

The instant process is normally conducted in the liquid phase at reaction temperatures of from about 20° to about 65° C. Most often, the reaction proceeds very satisfactorily at ambient temperatures.

The following examples will further illustrate the instant invention.

EXAMPLE 1

To a slurry of 1.63 g (0.025 mole) of finely powdered potassium hydroxide (85 percent) and 200 ml of bromochloromethane were added 6.13 g (0.025 mole) of 2,3,5,6-tetrachlorobenzenethiol. To this mixture, 0.30 g of benzyltriethylammonium bromide was added, and almost immediately the reaction mixture became turbid. The reaction mixture was slowly warmed to 55° C. over a period of 0.5 hour, and then cooled to room temperature. The reaction mixture was filtered to remove the potassium bromide by-product produced and the bromochloromethane was removed from the filtrate under reduced pressure leaving 8.0 g of a light yellow solid. The solid was dissolved in ether, and the solution dried over anhydrous magnesium sulfate and filtered. Hexane was added to the ether filtrate, and the resulting solution concentrated under reduced pressure to give 3.2 g of 2,3,5,6-tetrachlorophenyl chloromethyl sulfide as white platelets melting at 81° to 82° C. Further concentration gave an additional 2.9 g of the desired product. The combined total yield is 82 percent of theory.

Analysis: Calculated for $C_7H_3Cl_5S$: C, 28.36; H, 1.02; Cl, 59.80; S, 10.81. Found: C, 28.20; H, 1.06; Cl, 58.4; S, 11.10.

EXAMPLES 2-19

The Examples 2 thru 19 were conducted under essentially the same conditions as per Example 1 but with other combinations of reactants. The results of this series of experiments are summarized in Table I below.

TABLE I

| Ex. | Product | Yield (%) |
|---|---|---|
| 2 | F,F-substituted phenyl-SCH₂Cl | 84 |
| 3 | F,F,Cl,Cl-substituted phenyl-SCH₂Cl | 82 |
| 4 | Cl,Cl,Cl,Cl-substituted phenyl-SCH₂Cl | 49 |
| 5 | Cl,Cl,Cl,NO₂-substituted phenyl-SCH₂Cl | 63 |
| 6 | Br,Br,Br-substituted phenyl-SCH₂Cl | 91 |
| 7 | Cl,Cl,Cl-substituted phenyl-SCH₂Cl with SO₂N(C₂H₅)₂ | 83 |
| 8 | phenyl-SCH₂Cl | 57 |
| 9 | naphthyl-SCH₂Cl | 50 |
| 10 | t-C₄H₉-phenyl-SCH₂Cl | 60 |
| 11 | Cl,Cl,Cl-substituted pyridyl-SCH₂Cl | 78 |
| 12 | quinolinyl-SCH₂Cl | 43 |
| 13 | benzoxazolyl-SCH₂Cl | 80 |
| 14 | benzothiazolyl-SCH₂Cl | 58 |
| 15 | C₂H₅O-benzothiazolyl-SCH₂Cl | 93 |
| 16 | Cl-benzothiazolyl-SCH₂Cl | 97 |
| 17 | N-methyl-imidazolinyl-SCH₂Cl | 90 |

Note: The figure under "Yield (%)" in Table I represents an "in-hand" isolated product yield based on the reactants charged to the reaction.

Powdered sodium hydroxide was used in Example 16 instead of powdered potassium hydroxide. Lithium hydroxide is similarly useful, as evidenced by a 78 percent yield of 2,4,6-tribromophenyl chloromethyl sulfide when it was used in a reaction analogous to Example 6 above.

EXAMPLES 18–19

The products

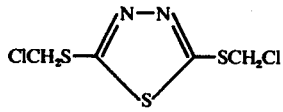

and

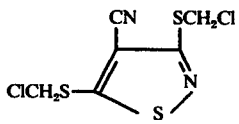

were produced in 71 and 60 percent yields, respectively, in similar experiments. However, in these experiments, the potassium aryl mercaptides were formed in a separate reaction, isolated, and subsequently reacted with bromochloromethane in the presence of benzyltriethylammonium chloride. These experiments were conducted to show that the reaction is operable starting with the mercaptide salts (rather than forming them in situ) and to show that aromatic compounds bearing more than one mercapto group per aromatic nuclei could be used in the process.

In each of Examples 1–19, the products were identified by infrared and/or nuclear magnetic resonance spectroscopy and by elemental analysis.

The above examples demonstrate the effectiveness of preparing aryl chloromethyl sulfides by the instant process. Other aromatic mercaptans and those used in the above examples can obviously be used as reactants in the process as can other benzylammonium salts as catalyst.

What is claimed is:

1. A process for preparing an aryl chloromethyl sulfide comprising reacting by contacting in liquid phase (a) an alkali metal aryl mercaptide with (b) bromochloromethane in the presence of (c) a small but sufficient amount of a quaternary ammonium salt to catalyze the reaction between (a) and (b); said quaternary ammonium salt having an aggregate carbon content of at least 10 carbon atoms.

2. The process defined by claim 1 wherein (c) is a quaternary ammonium salt having an aggregate carbon content of from about 12 to about 31 carbon atoms.

3. The process defined by claim 2 wherein (c) is a benzyltrimethyl-, a benzyltriethyl-, a tetra-n-butyl- or a tri-n-butylmethylammonium salt.

4. The process defined by claim 1 wherein (a) is formed in situ by reacting an aromatic mercaptan with an alkali metal hydroxide.

5. The process defined by claim 4 wherein said alkali metal hydroxide is sodium or potassium hydroxide.

6. The process defined by claim 5 wherein the reaction medium is liquid bromochloromethane.

7. The process defined by claim 6 wherein (c) is a benzyltrimethyl-, a benzyltriethyl-, a tetra-n-butyl- or a tri-n-butylmethylammonium salt.

8. The process defined by claim 1 wherein (a) is a sodium or potassium salt of a benzenethiol bearing fluorine, chlorine, or bromine on the aromatic ring.

9. The process defined by claim 1 wherein (a) is a sodium or potassium salt of 2,5-dimercapto-1,3,4-thiadiazole.

10. The process defined by claim 1 wherein (a) is a sodium or potassium salt of 4-cyano-3,5-dimercaptoisothiazole.

11. The process defined by claim 7 wherein (a) is a sodium or potassium salt of a tri- or tetrahalobenzenethiol, with the provision that said halo-substituents are fluorine, chlorine, or bromine.

12. The process defined by claim 7 wherein said aromatic mercaptan is a benzenethiol bearing fluorine, chlorine or bromine on the aromatic ring.

13. The process defined by claim 7 wherein said aromatic mercaptan is 2,5-dimercapto-1,3,4-thiadiazole.

14. The process defined by claim 7 wherein said aromatic mercaptan is 4-cyano-3,5-dimercaptoisothiazole.

* * * * *